United States Patent [19]

Fellmann et al.

[11] Patent Number: 4,536,589
[45] Date of Patent: Aug. 20, 1985

[54] POLYMERS OF FERROCENE

[75] Inventors: Jere D. Fellmann, Ashland; Philip E. Garrou, Holliston, both of Mass.; Howard P. Withers, Jr., Reading, Pa.; Dietmar Seyferth, Lexington, Mass.

[73] Assignee: The Dow Chemical Company, Midland, Mich.

[21] Appl. No.: 319,827

[22] Filed: Nov. 9, 1981

[51] Int. Cl.$^3$ .............................. C07F 9/66; C07F 9/90; C07F 17/02
[52] U.S. Cl. ......................................... 556/14; 556/19; 556/20; 556/30
[58] Field of Search ..................... 260/439 CY; 528/9

[56] References Cited

U.S. PATENT DOCUMENTS 3,238,185  3/1966  Neuse ........................... 260/439 CY
3,418,350  12/1968  Sollott et al. ................. 260/439 CY
4,138,420  2/1979  Unruh et al. ................. 260/439 CY

FOREIGN PATENT DOCUMENTS 55-2627  1/1980  Japan .
1537918  1/1979  United Kingdom .

OTHER PUBLICATIONS

Seyferth et al., J. Organometallic Chem. 185 $C_1$–$C_5$ (1980).
Sullivan et al., Organic Prep. and Proc. 2 (3), 159–159 (1970).
Bishop et al., J. Organometallic Chem. 27, 241–249 (1971).
Neuse et al., J. Macromol. Sci. (Chem.) A1 (3), 371–386 (1967).
Pittman, J. of Polymer Science PtA-1V5, 2927–2937 (1967).
Withers et al., Organometallics 1, 1283 (1983).

Primary Examiner—Helen M. S. Sneed
Attorney, Agent, or Firm—Douglas N. Deline

[57] ABSTRACT

Novel linear polymers of ferrocene are prepared by the reaction of 1,1'-dilithioferrocene with controlled amounts of a dihaloorganylphosphine, arsine or stibine. The polymers form stable complexes with Group VIII metals which are useful as recoverable hydroformylation catalysts.

8 Claims, No Drawings

POLYMERS OF FERROCENE

The U.S. Government and its agencies have a paid-up license in this invention as provided by the terms of Grant No. AFOSR 79-0007 awarded by the Air Force Office of Scientific Research, U.S. Department of the Air Force.

BACKGROUND OF THE INVENTION

The present invention relates to linear polymers of ferrocene and a process for making such polymers. The polymers are useful for the formation of novel metal chelates which are exceptionally stable catalysts for use in a hydroformylation process. Furthermore because of the highly linear nature of the ferrocene polymers, the catalysts are homogeneous under a wide variety of reaction conditions yet may be easily rendered insoluble for recovery purposes.

D. Seyferth and H. P. Withers in *Journal of Organometallic Chemistry*, 185, C1-5 (1980) disclosed certain mono- and bidentate ligands, including 1-diphenylarsino-1'-diphenylphosphinoferrocene. Also disclosed was the fact that phosphino- or arsinoferrocene polymers capped at one end with lithium and at the other end with an organic moiety can be prepared by reacting (1,1'-ferrocenediyl)phenylphosphine or (1,1'-ferrocenediyl)phenylarsine with a stoichiometric deficiency of an organolithium reagent. Subsequent efforts to produce high molecular weight polymeric materials by means of this process have resulted in oligomers of up to about five units but no higher polymeric materials have been observed.

The reaction of ferrocene with phenyldihalophosphines to produce polymeric products has been studied by C. U. Pittman, Jr., *J. Pol. Sci. A-1*, 5, 2927–2937 (1967), and E. W. Neuse et al., *J. Macromol. Sci. (Chem)* A-1, 3, 371–386 (1967). The polymers formed were of the formula:

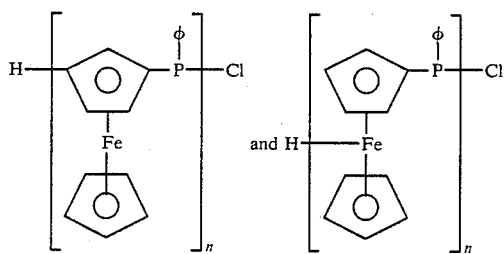

respectively.

The polymers formed were of relatively low molecular weight having number average molecular weights less than 4000 amu, and less than 6500 upon subfractionation. The polymers also were reported to contains cross-linking formed by the non-selective reaction of more than two phenyldihalophosphines with certain ferrocene moieties. The references further described "heteroannular polymerization", the process resulting from cleavage of ferrocene rings by the action of hydrogen chloride produced in situ and the subsequent incorporation of moieties other than ferrocene and phosphine into the polymer structure. The principal heteroannular moiety is cyclopentylene.

Polymers prepared according to the prior art processes by the Lewis acid-catalyzed polycondensation of ferrocene contained appreciable amounts of such cyclopentylene or related groups in the polymeric structure. The presence of such cyclopentylene groups in the polymer tends to reduce the polymer's thermal stability and otherwise deleteriously affect the polymer's qualities.

It would be desirable to produce a polymeric ferrocenyl derivative of relatively high molecular weight which is linear and which is substantially free from heteroannular polymerized moieties.

SUMMARY OF THE INVENTION

Accordingly, the present invention provides novel linear polymers of ferrocene having the formula

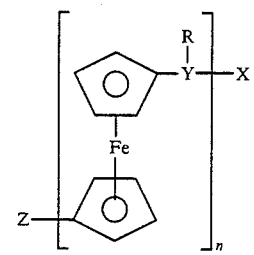

where R is a hydrocarbyl or oxy containing hydrocarbyl radical of up to about 10 carbons selected from alkyl, aryl, alkaryl, aralkyl, alkenyl, aralkenyl, alkoxy, aryloxy, and alkoxyaryl (hereinafter referred to as an organyl radical); Y is trivalent phosphorus, arsenic or antimony; X is halo, hydroxy, R or an ester group of up to about 10 carbons; Z is lithium, hydrogen or a group of the formula $Y(R)_2$ where Y and R are as previously defined; and n is an integer greater than 2. The polymers are prepared by a novel process comprising controllably reacting 1,1'-dilithioferrocene with a dihalo organyl phosphine, arsine or stibine under an inert atmosphere in a solvent or other liquid suitable for preparing the high molecular weight compounds. When prepared in this manner the resulting polymers contain substantially no cross-linking due to the preferential reactivity of the lithium reactive site. As previously mentioned, the high linearity of the invented polymers imparts important physical properties to the compounds.

The polymers of the invention have been found to be extremely useful in preparing supported metal catalysts. Typically, when employed in this manner, a homogeneous metal catalyst such as those containing a group VIII metal is bonded to the polymeric ferrocenyl derivatives of the invention thereby producing a novel catalyst system for use in either homogeneous or heterogeneous applications depending on the solvent system employed. Such supported catalysts have been found to be particularly stable at elevated temperatures and are useful in hydroformylation reactions. Preparation of such supported metal catalysts and their use in catalyzing hydroformylation reactions is further described in the copending application of Garrou and Fellmann, Ser. No. 319,826, filed Nov. 9, 1981.

DETAILED DESCRIPTION OF THE INVENTION

The polymeric compounds of the invention are prepared by controllably adding a suitably dilute solution of a dihaloorganylphosphine, arsine or stibine to a solution or slurry of 1,1'-dilithioferrocene. 1,1'-Dilithioferrocene is a known compound prepared, for example, by the reaction of n-butyllithium with ferrocene in a suitable solvent, in the presence of N,N,N',N'-tetramethylethylenediamine. The process has been previously described in Bishop et al., *J. Organometallic Chem.*, 27, 241-249 (1971).

The dihaloorganylphosphines, arsines and stibines employed in the invention are compounds of the formula $X_2YR$ where X is halo and Y and R are as previously defined. These are well-known compounds that may be commercially obtained or prepared by known methods. By halo is included fluoro, chloro, bromo and iodo. Preferred are the dihaloorganylphosphines. Preferred halo substituents are chloro. Preferred organyl substituents are phenyl or lower alkyl. A most preferred reactant is dichlorophenyl phosphine.

The addition is performed under carefully controlled circumstances due to the known pyrophoric nature of 1,1'-dilithioferrocene. An inert liquid that will form a solution or a slurry is employed. Suitable inert liquids are those compounds that are unreactive under the reaction conditions and which preferably substantially prevent precipitation of the polymeric material prior to formation of compounds of relatively high molecular weight. Suitable inert liquids include low molecular weight aromatic compounds such as toluene, xylenes, ethylbenzene, etc.; $C_{4-10}$ alkanes such as hexane, cyclohexane, heptane, etc.; and lower aliphatic ethers such as tetrahydrofuran, diethyl ether and diethers of alkylene or polyalkylene glycols.

Because both reactants may be oxygen sensitive, the reaction is conducted under an inert atmosphere thereby preventing oxidation which detrimentally affects polymer formation and the chelating ability of the polymer formed. A suitably inert atmosphere is produced by a blanket of nitrogen, argon or other inert gas in the reaction vessel. The reactor vessel may be of normal design and construction. Suitable materials include glass and glass lined metal reactors equipped with entry and exit means for the inert gas. The reaction may be conducted at temperatures from about −80° C. to about 100° C. or higher. Preferred temperatures are from about −10° C. to about 25° C.

The dihaloorganylphosphine, arsine or stibine reactant is purposely added in a controlled manner and as a dilute solution accompanied by agitation of the reaction mixture in order that the intermediate may further react primarily with additional molecules of dilithioferrocene thereby forming polymeric reaction products. Dimers are formed if the intermediate reacts with another intermediate. Such dimers are of limited utility in the formation of hydroformylation catalysts by complexation with metals since the resulting catalyst is homogeneous and not easily recoverable from the reaction mixture. Formation of the polymers as well as the undesirable dimers is illustrated pictorially by the following schematic drawing of the process:

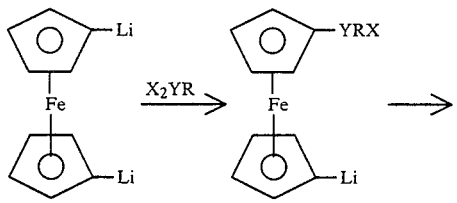

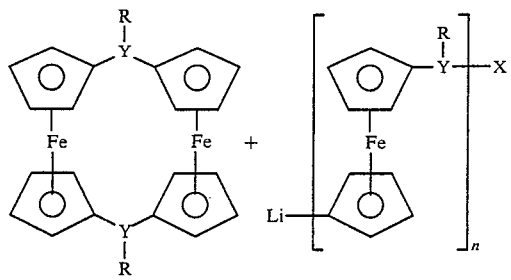

where X is halo and R, Y, and n are as previously defined.

The polymers may be easily hydrolyzed by reaction with water or an alcohol thereby removing the lithium moiety and capping the polymer at one end with hydrogen and at the other end removing the halogen and capping the polymer with a hydroxyl or an alkyl ether moiety. Alternatively, the halogen moiety may be reacted with an acid of up to about 10 carbons thereby producing ester functionality. In this manner acrylic, methacrylic, or other similarly functionalized ester group may be incorporated into the polymers. The halogen of the invented polymers may additionally be removed by known techniques, e.g., alkylation by reaction with an alkali metal compound such as phenyllithium, alkyllithium or ferrocenyllithium, thereby producing organyl terminated polymers. Alternatively, the halogen moiety may be reacted with alkali metal alkoxides or phenoxides according to a Williamson synthesis to give esters. The lithium moiety may be removed in similar manner by reaction with a dihydrocarbyl halo phosphine, arsine or stibine thereby forming a polymer terminated by a dihydrocarbyl phosphine group. Capping of the polymers of the invention according to these techniques is preferred in order to reduce the amount of lithium and particularly chlorine functionality in the polymer thereby reducing the number of groups which may interfere with the catalytic properties of the metal chelated compounds. However, suitable catalysts may be produced without the necessity of such capping operations particularly where the polymers are of sufficiently high molecular weight that the terminal halogen functionality is of minimal effect.

Polymers according to the invention may be produced by the above-described manner having very high absolute molecular weights. Preferred polymers are those of from about 4,000 to about 200,000 amu, and most preferably of from about 8,000 to about 160,000 amu. In measuring such absolute molecular weights, the technique of low angle laser light scattering is employed.

The polymeric ferrocene derivatives of the invention may be easily reacted with metal compounds to produce supported metal complexes, according to known techniques taught, for example, in U.S. Pat. Nos. 4,098,727; 4,045,493 and 3,239,569, which teachings are incorporated herein by reference.

Accordingly, the polymeric ferrocene derivatives are contacted with metal compounds selected from compounds of metals of Group VIII of the Periodic Table that are capable of forming complexes with the hydrocarbyl phosphine, arsine or stibine functionality of the invention polymers by means of ligand exchange. Suitable compounds include, for example, the carbonyl or halide derivatives of such metals. Preferred metal compounds are the metal carbonyls, particularly dicobalt octacarbonyl.

The supported metal complexes are preferably prepared under an inert atmosphere to prevent detrimental oxidation of the reactants and in a suitable inert liquid such as the hydrocarbons and ethers previously mentioned for formation of the ferrocene polymers. Preferred inert liquids include lower dialkyl ethers, tetrahydrofuran, etc.

The supported metal complex may be employed in known reactions are a chelated metal catalyst is known to be suitably employed. The molecular weight of the polymer employed in preparing the supported metal complex catalysts will in part determine the ease of recovery of the catalysts from reaction processes. The greater the molecular weight of the original polymeric ferrocene derivative to which the metal compounds are chelated, the more tractable and easily recoverable are the resulting supported metal catalysts.

Use of the supported metal catalysts in hydroformylation processes is accomplished employing conventional techniques such as are taught, for example, in U.S. Pat. No. 4,045,493. The catalyst may first be recovered from the inert liquid wherein it was prepared if desired and then employed in the production of aldehydes and alcohols by contacting an olefinic hydrocarbon with carbon monoxide and hydrogen in the presence of the catalyst under conditions well-known for the hydroformylation reaction. Typically, reaction conditions comprising temperatures in the range of about 100° C. to about 300° C. and pressures in the range of about 10 to about 2000 psig are utilized.

The amount of catalyst to be used in the reaction is not critical and may vary over a wide range, for example, olefin to catalyst weight ratios between 500:1 and 1:1 are suitable. Particularly suitable are olfein to catalyst weight ratios ranging from about 20:1 to about 5:1.

Olefins containing 4 to 19 carbon atoms, particularly those containing 6 to 10 carbon atoms are feedstocks that can be utilized advantageously. Under the conditions of the hydroformylation reaction, the olefins are converted to aldehydes and alcohols having one more carbon atom than the olefin charged.

The mole ratios of hydrogen to carbon monoxide employed may vary widely, for example, over the range of about 1:1 to about 10:1. The specific ratio to be used will be governed in part by the nature of the reaction products desired. For example, if an aldehyde product is desired, a suitable mole ratio of hydrogen to carbon monoxide is 1:1; if an alcohol is the desired product, a suitable mole ratio is 2:1.

The liquid reaction products are readily separated from the catalyst by adding a non-solvent for the catalyst such as hexane and filtering. The products may be purified by distillation or other conventional means.

SPECIFIC EMBODIMENTS

Having described the invention, the following examples are provided as further illustrative but are not to be construed as limiting.

EXAMPLE 1

Preparation of Polymer

A 300 ml, three-necked, Morton flask was charged with 1,1'-dilithioferrocene as a complex with tetramethylethylenediamine (5.17 g, 0.0163 mole) while in a glove box and then fitted with a mechanical stirrer, a pressure equalizing dropping funnel, a gas inlet tube and a no-air stopper. The apparatus was removed from the glove box and connected to a Schlenk manifold. Hexane (approx. 200 ml) was added to the dilithioferrocene under nitrogen atmosphere by cannula. Dichlorophenylphosphine (2.04 ml, 0.015 mole) and hexane (60 ml) were added to the funnel by syringe.

The solution in the funnel was added dropwise over about 1 hour to the vigorously stirred dilithioferrocene/hexane slurry at room temperature. The resulting tan-orange mixture was stirred overnight at room temperature. The reaction mixture was treated with 10 ml of water and stirred for 30 minutes. It was then filtered in air, and the tan solid washed with 2×50 ml portions of hexane. The red filtrate was discarded. The tan solid was extracted with 100 ml of dichloromethane under nitrogen. The extract was dried over $MgSO_4$, filtered, and the solvent removed in vacuo to give 1.87 g (43 percent conversion) of a glassy, brown solid. Further purification of the polymer was afforded by precipitation of a dichloromethane solution of the polymer into a large volume of rapidly stirred pentane. This gave a very fluffy, tan solid. A more easily handled material could be obtained by dissolving the polymer in dichloromethane and removing the dichloromethane at reduced pressure to yield a brown, glassy, brittle solid. The solid was identified as poly[1,1'-ferrocenylene(phenylphosphine)] by standard techniques of infrared spectroscopy, $^{31}P$ and $^1H$ nuclear magnetic resonance spectroscopy. Thermogravimetric analysis indicated 55.8 percent total weight loss at temperature above 390° C.

Absolute molecular weight was found to be 47,000 amu as determined by low angle laser light scattering using a Chromatix KMX-6 instrument.

EXAMPLE 2

The reaction conditions of Example 1 were substantially repeated employing 1,2-dimethoxyethane solvent. Hydrolysis was accomplished by addition of saturated aqueous ammonium chloride solution. The produce was again identified by standard analytical techniques as poly[1,1'-ferrocenylene(phenylphosphine)]. Absolute molecular weight was determined to be 8,900 amu.

EXAMPLE 3

The reaction conditions of Example 1 were again repeated employing diethylether as the solvent. The product was poly[1,1'-ferrocenyl(phenylphosphine)] having an absolute molecular weight of 161,000 amu.

EXAMPLE 4

Preparation of cobalt catalyst

The poly[1,1'-ferrocenylene(phenylphosphine)] prepared in Example 2 (80 mg) was combined in 20 ml of tetrahydrofuran with $Co_2(CO)_8$ (40 mg). A homogeneous solution was formed. Upon addition of a mixture of 1-hexene (4.0 g) and n-decane (1.0 g), the catalyst precipitated resulting in a nearly colorless solution.

EXAMPLE 5

Hydroformylation process

The mixture of Example 4 was placed in a stirred autoclave purged with argon and pressurized with a 1:2 mixture of $CO:H_2$ to 1600 psig and heated to 190° C. to a total pressure of 2000 psig. The mixture was vigorously stirred for 10 hours. The reaction was discontinued and the resulting mixture analyzed by gas-liquid chromatography. Results are contained in Table I. Conversion of hexene was more than 99 percent.

TABLE I

| Component | mole % |
|---|---|
| n-hexane | 4.6 |
| C$_7$ aldehydes | 8.4 |
| C$_7$ alcohols | 77.0 |
| heptyl formate | 1.6 |

What is claimed is:

1. A linear polymer of ferrocene substantially free from heteroannular moieties having an absolute molecular weight from about 8.000 to about 160,000 amu having the formula:

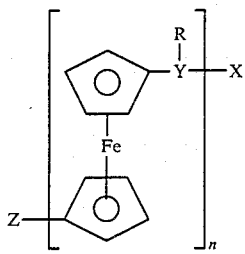

where R is a hydrocarbyl or an oxy containing hydrocarbyl radical of up to about 10 carbons selected from the group consisting of alkyl, aryl, alkaryl, aralkyl, alkenyl, aralkenyl, alkoxy, aryloxy and alkoxyaryl radicals; Y is triavalent phosphorus, arsenic or antimony; X is halo, hydroxy, R, or an ester group of up to about 10 carbons; Z is lithium, hydrogen or a group of the formula Y(R)$_2$ where Y and R are as previously defined; and n is an integer greater than 2.

2. A process for producing linear polymers of ferrocene corresponding to the formula

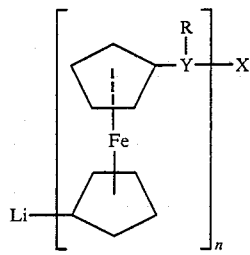

where R is a hydrocarbyl or hydrocarboxyl radical of up to about 10 carbons selected from the group consisting of alkyl, aryl, alkaryl, aralkyl, alkenyl, aralkenyl, alkoxy, aryloxy and alkoxyaryl radicals; Y is trivalent phosphorus, arsenic or antimony; X is halo; and n is an integer greater than 2, comprising reacting 1,1'-dilithioferrocene with a reactive compound of formula X$_2$YR where X, Y and R are as previously defined, by controllably adding the reactive compound to the 1,1'-dilithioferrocene at a rate such that formation of dimer byproducts is substantially avoided.

3. The process according to claim 2 wherein Y is trivalent phosphorus.

4. The process according to claim 3 wherein X is chloro.

5. The process according to claim 3 wherein the reactants are present in an inert liquid.

6. The process according to claim 5 wherein the inert liquid is a low molecular weight aromatic compound, a C$_{4\text{-}10}$ alkane, or a lower aliphatic ether.

7. The process according to claim 2 wherein the reaction is conducted at temperatures from about −80° C. to about 100° C.

8. The process according to claim 7 wherein the temperature is from about −10° C. to about 25° C.

* * * * *